(12) United States Patent
Durschang et al.

(10) Patent No.: US 9,604,873 B2
(45) Date of Patent: *Mar. 28, 2017

(54) LITHIUM DISILICATE GLASS-CERAMIC, METHOD FOR PRODUCTION THEREOF AND USE THEREOF

(71) Applicants: FRAUNHOFER-GESELLSCHAFT zur Förderung der angewandten Forschung e.V., München (DE); VITA Zahnfabrik H. Rauter GmbH & Co. KG, Bad Säckingen (DE); DeguDent GmbH, Hanau (DE)

(72) Inventors: Bernhard Durschang, Rottendorf (DE); Jörn Probst, Kürnach (DE); Norbert Thiel, Bad Säckingen (DE); Joachim Bibus, Bad Säckingen (DE); Markus Vollmann, Gelnhausen (DE); Udo Schusser, Alzenau (DE)

(73) Assignees: Fraunhofer-Gesellschaft zur förderung der angewandten Forschung e.V., München (DE); Vita Zahnfabrik H. Rauter GmbH & Co. KG, Bad Sackingen (DE); DeguDent GmbH, Hanau (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/586,229

(22) Filed: Dec. 30, 2014

(65) Prior Publication Data
US 2015/0246843 A1 Sep. 3, 2015

Related U.S. Application Data

(63) Continuation of application No. 13/518,765, filed as application No. PCT/EP2010/007918 on Dec. 23, 2010, now Pat. No. 8,956,987.

(30) Foreign Application Priority Data

Dec. 23, 2009 (DE) .................. 10 2009 060 274

(51) Int. Cl.
| | |
|---|---|
| *C03C 10/04* | (2006.01) |
| *C03C 10/00* | (2006.01) |
| *A61K 6/02* | (2006.01) |
| *A61K 6/027* | (2006.01) |
| *C03B 32/02* | (2006.01) |
| *A61C 5/08* | (2006.01) |
| *A61C 13/083* | (2006.01) |
| *A61C 5/00* | (2017.01) |
| *A61C 5/10* | (2006.01) |
| *A61C 13/00* | (2006.01) |
| *A61C 13/01* | (2006.01) |

(52) U.S. Cl.
CPC .......... *C03C 10/0009* (2013.01); *A61C 5/005* (2013.01); *A61C 5/08* (2013.01); *A61C 5/10* (2013.01); *A61C 13/0006* (2013.01); *A61C 13/01* (2013.01); *A61C 13/083* (2013.01); *A61K 6/024* (2013.01); *A61K 6/0245* (2013.01); *A61K 6/0273* (2013.01); *C03B 32/02* (2013.01); *C03C 10/0027* (2013.01)

(58) Field of Classification Search
CPC . C03C 10/0009; C03C 10/0027; A61L 27/10; A61C 13/083
See application file for complete search history.

(56) References Cited

U.S. PATENT DOCUMENTS

| | | | |
|---|---|---|---|
| 2,684,911 | A | 7/1954 | Stookey |
| 3,238,085 | A | 3/1966 | Hayami et al. |
| 4,515,634 | A | 5/1985 | Wu et al. |
| 5,507,981 | A | 4/1996 | Petticrew |
| 5,698,482 | A | 12/1997 | Frank et al. |
| 5,925,180 | A | 7/1999 | Frank et al. |
| 5,968,856 | A | 10/1999 | Schweiger et al. |
| 6,268,303 | B1 | 7/2001 | Aitken et al. |
| 6,420,286 | B1 | 7/2002 | Goto et al. |
| 6,420,288 | B2 | 7/2002 | Schweiger et al. |
| 6,426,311 | B1 | 7/2002 | Goto et al. |
| 6,524,982 | B1 | 2/2003 | Nagata et al. |
| 6,703,332 | B2 | 3/2004 | Peng et al. |
| 7,166,548 | B2 | 1/2007 | Apel et al. |

(Continued)

FOREIGN PATENT DOCUMENTS

| | | |
|---|---|---|
| AU | 2011-325524 A1 | 4/2013 |
| CA | 2213390 A1 | 3/1998 |

(Continued)

OTHER PUBLICATIONS

Borom et al., "Strength and Microstructure in Lithium Disilicate Glass-Ceramics", *Journal of the American Ceramic Society*, vol. 58, No. 9-10, pp. 385-391 (1975).
De Oliveira et al., "Sintering and Crystallization of a Glass Powder in the $Li_2O$—$ZrO_2$—$SiO_2$ System," *Communications of the American Ceramic Society*, vol. 81, No. 3, pp. 777-780 (1998).
Montedo et al. "Low Thermal Expansion Sintered LZSA Glass-Ceramics," *American Ceramic Society Bulletin*, vol. 87. No. 7, pp. 34-40 (2008).
Stookey, "Chemical Machining of Photosensitive Glass", *Industrial and Engineering Chemistry*, 45, pp. 115-118 (1993).

(Continued)

*Primary Examiner* — Karl Group
(74) *Attorney, Agent, or Firm* — Leydig, Voit & Mayer, Ltd.

(57) ABSTRACT

The invention relates to glass-ceramics based on the lithium disilicate system which can be mechanically machined easily in an intermediate step of crystallization and, after complete crystallization, represent a very strong, highly-translucent and chemically-stable glass-ceramic. Likewise, the invention relates to a method for the production of these glass-ceramics. The glass-ceramics according to the invention are used as dental material.

11 Claims, No Drawings

(56) References Cited

U.S. PATENT DOCUMENTS

| | | |
|---|---|---|
| 7,452,836 B2 | 11/2008 | Apel et al. |
| 7,867,930 B2 | 1/2011 | Apel et al. |
| 7,867,931 B2 | 1/2011 | Apel et al. |
| 7,867,933 B2 | 1/2011 | Apel et al. |
| 7,871,948 B2 | 1/2011 | Apel et al. |
| 7,892,995 B2 | 2/2011 | Castillo |
| 7,993,137 B2 | 8/2011 | Apel et al. |
| 8,162,664 B2 | 4/2012 | Apel et al. |
| 8,536,078 B2 | 9/2013 | Ritzberger et al. |
| 8,546,280 B2 | 10/2013 | Apel et al. |
| 8,557,150 B2 | 10/2013 | Ritzberger et al. |
| 8,592,330 B2 | 11/2013 | Johannes et al. |
| 8,759,237 B2 | 6/2014 | Ritzberger et al. |
| 8,778,075 B2 | 7/2014 | Ritzberger et al. |
| 8,956,987 B2* | 2/2015 | Durschang ............... 106/35 |
| 9,125,812 B2* | 9/2015 | Durschang ............ C03C 3/097 |
| 9,206,077 B2* | 12/2015 | Durschang ............ C03B 32/02 |
| 2002/0010063 A1 | 1/2002 | Schweiger et al. |
| 2005/0098064 A1 | 5/2005 | Schweiger et al. |
| 2005/0209082 A1 | 9/2005 | Apel et al. |
| 2007/0042889 A1 | 2/2007 | Apel et al. |
| 2009/0038344 A1 | 2/2009 | Apel et al. |
| 2009/0038508 A1 | 2/2009 | Apel et al. |
| 2009/0042713 A1 | 2/2009 | Apel et al. |
| 2009/0042714 A1 | 2/2009 | Apel et al. |
| 2009/0256274 A1 | 10/2009 | Castillo |
| 2010/0083706 A1 | 4/2010 | Castillo |
| 2011/0030423 A1 | 2/2011 | Johannes et al. |
| 2011/0059836 A1 | 3/2011 | Apel et al. |
| 2011/0252831 A1 | 10/2011 | Apel et al. |
| 2011/0256409 A1 | 10/2011 | Ritzberger et al. |
| 2011/0257000 A1 | 10/2011 | Ritzberger et al. |
| 2011/0259053 A1 | 10/2011 | Apel et al. |
| 2012/0248642 A1 | 10/2012 | Ritzberger et al. |
| 2012/0309607 A1* | 12/2012 | Durschang ............ A61K 6/024 501/59 |
| 2013/0295523 A1 | 11/2013 | Durschang et al. |
| 2013/0296156 A1 | 11/2013 | Apel et al. |
| 2013/0323404 A1 | 12/2013 | Ritzberger et al. |
| 2014/0000314 A1 | 1/2014 | Ritzberger et al. |
| 2014/0200129 A1 | 7/2014 | Durschang et al. |
| 2014/0249016 A1 | 9/2014 | Durschang et al. |
| 2014/0252272 A1 | 9/2014 | Durschang et al. |
| 2014/0335473 A1 | 11/2014 | Ritzberger et al. |

FOREIGN PATENT DOCUMENTS

| | | |
|---|---|---|
| CA | 2252660 A1 | 5/1999 |
| CN | 1306946 A | 8/2001 |
| DE | 14 21 886 A1 | 6/1969 |
| DE | 24 51 121 A1 | 5/1975 |
| DE | 19750794 A1 | 6/1999 |
| DE | 10 2004 013455 B3 | 9/2005 |
| DE | 10 2005 028637 A1 | 12/2006 |
| DE | 10 2007 011337 A1 | 9/2008 |
| DE | 10 2009 060274 A1 | 6/2011 |
| DE | 102010050275 A1 | 5/2012 |
| EP | 0 536 572 A1 | 4/1993 |
| EP | 0 536 479 B1 | 9/1995 |
| EP | 0 690 031 A1 | 1/1996 |
| EP | 0 827 941 A1 | 3/1998 |
| EP | 0 916 625 A1 | 5/1999 |
| EP | 1 505 041 A1 | 2/2005 |
| EP | 1 688 397 A1 | 8/2006 |
| EP | 2 305 614 A2 | 4/2011 |
| EP | 2 377 831 A1 | 10/2011 |
| FR | 2 655 264 A | 6/1991 |
| JP | S58-120539 A | 7/1983 |
| JP | H08-040744 A | 2/1996 |
| JP | H10-101409 A | 4/1998 |
| JP | H11-314938 A | 11/1999 |
| JP | 2001-019468 A | 1/2001 |
| JP | 2005-053776 A | 3/2005 |
| JP | 2005-062832 A | 3/2005 |
| JP | 2006-219367 A | 8/2006 |
| JP | 2011-225441 A | 11/2011 |
| JP | 2013-515659 A | 5/2013 |
| SU | 908 355 A1 | 2/1982 |
| WO | WO 95/32678 A2 | 12/1995 |
| WO | WO 2009/126317 A1 | 10/2009 |
| WO | WO 2011/076422 A1 | 6/2011 |
| WO | WO 2012/059143 A1 | 5/2012 |
| WO | WO 2012/175450 A1 | 12/2012 |
| WO | WO 2012/175615 A1 | 12/2012 |

OTHER PUBLICATIONS

Von Clausbruch et al., "Crystallization, Microstructure and Properties of Selected Glasses and Glass-Ceramics in the $SiO_2$—$Li_2O$—$ZnO$—$K_2O$—$P_2O_5$ System," *DGG Journal*, vol. 1, No. 1, pp. 41-49 (2002).

Australian Patent Office, Patent Examination Report No. 1 in Australian Patent Application No. 2010335472 (Mar. 4, 2014).

State Intellectual Property Office of the People's Republic of China, Second Office Action in Chinese Patent Application No. 201080063038.3 (Sep. 16, 2014).

State Intellectual Property Office of the People's Republic of China, Third Office Action in Chinese Patent Application No. 201080063038.3 (Jun. 3, 2015).

State Intellectual Property Office of the People's Republic of China, Fourth Office Action in Chinese Patent Application No. 201080063038.3 (Nov. 19, 2015).

Canada Intellectual Property Office, Examination Report in Canadian Patent Application No. 2,785,348 (Apr. 25, 2016).

Höland et al., "Control of nucleation in glass ceramics," *Phil. Trans. R. Soc. Lond. A*, 361: 575-589 (2003).

Höland et al., Glass-Ceramic Technology. The American Ceramic Society, Westerville, OH, Chapter 2: "Composition Systems for Glass-Ceramics," pp. 75-83; Chapter 3, section 3.4.1 "Chemical System and Crystalline Phases," and 3.4.2 "Determination of Crystal Phases," pp. 222-223 (2002).

Livingston et al., "Examination of the laser-induced variations in the chemical etch rate of a photosensitive glass ceramic," *Appl. Phys. A* 89: 97-107 (2007).

Zheng Xin, China Doctoral Dissertations Full-text Database, Engineering Science and Technology I, No. 12, Abstract only, publication date: Dec. 15, 2008.

State Intellectual Property Office of the People'S Republic of China, First Office Action in Chinese Patent Application No. 201080063038.3 (Apr. 2, 2014).

Durschang, "Comparison US2007/0042889 Example 2—ZLS Glass Ceramic 637-ZO Results Report," Fraunhofer-Institut für Silicatforschung ISC, Würzburg, Germany, Nov. 2, 2015 (6 pgs.).

Korean Intellectual Property Office, Notification of Reason for Refusal in Korean Patent Application No. 10-2012-7019057 (Oct. 24, 2016).

* cited by examiner

LITHIUM DISILICATE GLASS-CERAMIC, METHOD FOR PRODUCTION THEREOF AND USE THEREOF

CROSS-REFERENCE TO RELATED APPLICATIONS

This patent application is a continuation of copending U.S. patent application Ser. No. 13/518,765, filed Aug. 15, 2012, which is the U.S. national phase of International Application No. PCT/EP2010/007918, filed on Dec. 23, 2010, which claims the benefit of German Patent Application No. DE 10 2009 060 274.7, filed on Dec. 23, 2009, the disclosures of which are incorporated by reference in their entireties for all purposes.

BACKGROUND OF THE INVENTION

The invention relates to glass-ceramics based on the lithium disilicate system which can be mechanically machined easily in an intermediate step of crystallisation and, after complete crystallisation, represent a very strong, highly-translucent and chemically-stable glass-ceramic. Likewise, the invention relates to a method for the production of these glass-ceramics. The glass-ceramics according to the invention are used as dental material.

Lithium disilicate glass-ceramics are well known from the literature and several patents are based on this glass-ceramic system. Thus, for example, self-glazed lithium disilicate glass-ceramic objects for the production of tableware are described in EP-B-536 479, in EP-B-536 572 lithium disilicate glass-ceramics which can be used, by scattering fine-particle coloured glass on the surface thereof, as lining elements for building purposes.

The main focus of patented lithium disilicate glass-ceramics is on dental applications. This is due to the fact that the crystallisation of lithium disilicate crystals is effected via a phase of lesser strength (lithium metasilicate) and the material system is consequently amenable inter alia to chair-side methods (see S. D. Stookey: "Chemical Machining of Photosensitive Glass", Ind. Eng. Chem., 45, pp. 115-118 (1993) and S. D. Stookey: "Photosensitively Opacifiable Glass" U.S. Pat. No. 2,684,911 (1954)). Investigations by Borom, e.g. M. P. Borom, A. M. Turkalo, R. H. Doremus: "Strength and Microstructure in Lithium Disilicate Glass-Ceramics", J. Am. Ceram. Soc., 58, No. 9-10, pp. 385-391 (1975) and M. P. Borom, A. M. Turkalo, R. H. Doremus: "Verfahren zum Herstellen von Glaskeramiken" (Method for the production of glass-ceramics), DE-A-24 51 121 (1974) show that glass-ceramics which comprise lithium metasilicate as main phase have reduced strength in comparison with glass-ceramics which comprise lithium disilicate as single crystalline phase.

This principle was used in order firstly to produce a glass-ceramic, in a two-step crystallisation process, which can be machined well mechanically, e.g. by means of CAD/CAM methods, and to process this subsequently in a second crystallisation step to form dental glass-ceramic. This method is suitable for being able to use dental restorations according to the so-called chair-side method. In the case of this method, an individually adapted crown/onlay/inlay is milled out of a glass-ceramic block after the first crystallisation step by means of CAD/CAM in the dentist's surgery, this is subjected to the second crystallisation step in a special oven and used directly in the first and only dental appointment for the patient (DE 10 2005 028 637).

In addition, in WO-A-95/32678 and U.S. Pat. No. 5,507,981, lithium disilicate glass-ceramics were described, which can be processed to form shaped dental products by means of hot-pressing by using a special compressible crucible. Furthermore, there are known, from DE-C-14 21 886, glass-ceramics based on $SiO_2$ and $Li_2O$ which contain large quantities of physiologically very questionable arsenic oxide. Also in U.S. Pat. No. 4,515,634 and in FR-A-2 655 264, lithium disilicate glass-ceramics which are suitable for the production of dental crowns and bridges are disclosed.

All known lithium disilicate glass-ceramics display inadequacies in the processing thereof to shaped products and/or in mechanical or visual properties and/or in chemical stability. In particular when used in the dental field, equally high requirements for all the mentioned properties must be fulfilled.

BRIEF SUMMARY OF THE INVENTION

Starting herefrom, it was the object of the present invention to provide a glass-ceramic which has improved mechanical and optical properties and also improved chemical stability relative to the (glass-) ceramics known from the state of the art.

This object is achieved by the described lithium disilicate glass-ceramic, by the method for the production of this glass-ceramic, and the shaped dental product. Advantageous developments and uses of the invention are also described.

DETAILED DESCRIPTION OF THE INVENTION

The present invention provides a lithium disilicate glass-ceramic comprising at least 10% by weight of a stabiliser in order to increase the chemical and mechanical stability, the stabiliser being present essentially in the amorphous phase.

In the above lithium disilicate glass-ceramic embodiment, the stabiliser is selected from the group consisting of zirconium oxide, hafnium oxide and mixtures thereof.

Embodiments of the above lithium disilicate glass-ceramic have the following composition:
- 55 to 70% by weight of $SiO_2$,
- 10 to 15% by weight of $Li_2O$,
- 10 to 20% by weight of the stabiliser selected from the group consisting of $ZrO_2$, $HfO_2$ or mixtures hereof,
- 0.1 to 5% by weight of $K_2O$,
- 0.1 to 5% by weight of $Al_2O_3$,
- 0 to 10% by weight of additives and also
- 0 to 10% by weight of colourants.

In accordance with embodiments of the invention, the colourants are glass-colouring oxides and/or pigments.

In accordance with embodiments of the invention, the glass-colouring oxides are selected from the group of the oxides of iron, titanium, cerium, copper, chromium, cobalt, nickel, manganese, selenium, silver, indium, gold, rare earth metals, in particular neodymium, praseodymium, samarium and europium.

In any of the above embodiments, the pigments are doped spinels.

In any of the above embodiments, the additives are selected from the group consisting of boron oxide, phosphorus oxide, fluorine, sodium oxide, barium oxide, strontium oxide, magnesium oxide, zinc oxide, calcium oxide, yttrium oxide, titanium oxide, niobium oxide, tantalum oxide, lanthanum oxide and mixtures thereof In accordance with an embodiment, the lithium disilicate glass-ceramic has the following composition:

58 to 64% by weight of $SiO_2$,
11 to 13% by weight of $Li_2O$,
10 to 15% by weight of the stabiliser selected from the group consisting of $ZrO_2$, $HfO_2$ or mixtures thereof,
2 to 5% by weight of $K_2O$,
2 to 5% of $Al_2O_3$,
2 to 5% of $P_2O_5$ and also
0 to 5% by weight of additives and also
0 to 10% by weight of colourants.

In a specific embodiment, the invention provides a lithium disilicate glass-ceramic having the following composition:
55 to 70% by weight of $SiO_2$,
10 to 15% by weight of $Li_2O$,
10 to 20% by weight of the stabiliser selected from the group consisting of $ZrO_2$, $HfO_2$ and mixtures thereof,
0.1 to 5% by weight of $K_2O$,
0.1 to 5% by weight of $Al_2O_3$,
0 to 10% by weight of additives selected from the group consisting of boron oxide, phosphorus oxide, fluorine, sodium oxide, barium oxide, strontium oxide, magnesium oxide, zinc oxide, calcium oxide, yttrium oxide, titanium oxide, niobium oxide, tantalum oxide, lanthanum oxide and mixtures thereof, and
0 to 10% by weight of colourants.

In a further specific embodiment, the invention provides a lithium disilicate glass-ceramic having the following composition:
58 to 64% by weight of $SiO_2$,
11 to 13% by weight of $Li_2O$,
10 to 15% by weight of the stabiliser selected from the group consisting of $ZrO_2$, $HfO_2$ and mixtures thereof,
2 to 5% by weight of $K_2O$,
2 to 5% of $Al_2O_3$,
2 to 5% of $P_2O_5$ and
0 to 5% by weight of additives selected from the group consisting of boron oxide, phosphorus oxide, fluorine, sodium oxide, barium oxide, strontium oxide, magnesium oxide, zinc oxide, calcium oxide, yttrium oxide, titanium oxide, niobium oxide, tantalum oxide, lanthanum oxide and mixtures thereof, and
0 to 10% by weight of colourants.

The present invention further provides a method for the production of a lithium disilicate glass-ceramic as described above, in which
a) an initial glass is produced which comprises the components of the glass-ceramic,
b) the initial glass is subjected to a first heat treatment in order to produce a glass-ceramic which has lithium metasilicate as main crystal phase,
c) the glass-ceramic of b) is subjected to a second heat treatment in which the lithium metasilicate is converted with $SiO_2$ from the initial glass phase into lithium disilicate and subsequently lithium disilicate is present as main crystal phase.

In an embodiment of the above method, the first heat treatment is effected at a temperature of 620° C. to 800° C. over a period of time of 1 to 200 min, in particular, at a temperature of 650° C. to 750° C. over a period of time of 10 to 60 min.

In an embodiment of the above method, the second heat treatment is effected at a temperature of 800° C. to 1,040° C. over a period of time of 5 to 200 min, in particular at a temperature of 650° C. to 750° C. over a period of time of 5 to 30 min.

In accordance with an embodiment, the rare earth metals of the glass-colouring oxides are selected from the group consisting of neodymium, praseodymium, samarium and europium.

The lithium disilicate glass-ceramic as described above find use as dental material or as component of a dental material.

The present invention further provides a shaped dental product comprising a lithium disilicate glass-ceramic as described above, in particular in the form of an inlay, an onlay, a bridge, a pin construction, a veneer, a (partial) crown.

Within the scope of the present invention, glass compositions have been developed which can be prepared in a two-step production process, are easy to machine after the first crystallisation step, in particular by means of CAD/CAM, and, after a very short second crystallisation step, are both highly-transparent and very strong and have better chemical stabilities than the known lithium disilicate glass-ceramics.

It was shown surprisingly that the addition of $ZrO_2$ to certain glass compositions leads to glass-ceramics which can be machined very readily in an intermediate crystallisation step and, in the end state, have excellent strength values, exceptional translucence and significantly increased chemical stabilities.

It was shown that up to 20% by weight of a stabiliser selected from the group consisting of $ZrO_2$, $HfO_2$ or mixtures hereof can be incorporated in the glass without having a significant influence on the structure. Contrary to all expectations, the stabiliser does not hereby crystallise out as a separate crystal phase but remains in the remaining glass phase. As a result of the high proportion in the amorphous phase, the mechanical and chemical stabilities in this phase are hugely improved, which also leads to improved properties in the end product.

In particular the chemical stability can be improved via the composition of the remaining glass phase since the glass phase has a significantly higher solubility than the lithium disilicate and hence represents the weak point with respect to chemical attack. The extremely high solubility of the stabiliser ($ZrO_2$) in the glass phase is in particular remarkable since e.g. zirconium oxide acts in many silicate glass-ceramics as nucleation agent, i.e. crystallises out as first phase during a temperature treatment, and the actually sought crystal phase is facilitated and is deposited in a fine-crystalline manner on these $ZrO_2$ crystals.

As a result of the high proportions of stabiliser which remain essentially in the amorphous phase, the crystalline proportion is correspondingly restricted. As a result, and due to the low crystallite size of the lithium disilicate crystals, good translucence of the materials is produced after the second crystallisation. The translucence is however also further improved by the refractive index of the glass phase being increased in turn by the stabiliser and, consequently, being adapted to the refractive index of the lithium disilicate. In the case of glass-ceramics in which the refractive index of the amorphous matrix phase corresponds to the refractive index of the crystalline phase/phases, very good translucence properties are found, relatively irrespective of the crystallite size. In the glass-ceramics according to the invention, therefore all three points for the production of an extremely translucent glass-ceramic are fulfilled:
limited crystal phase proportion,
small crystals (<500 nm),
adapted refractive index of amorphous and crystalline phase.

The high proportion of stabiliser has the effect therefore in the glass-ceramic of
improved chemical stability,
higher strength values and
improved translucence in several respects
to corresponding glass-ceramics without or with only a low $ZrO_2$— or $HfO_2$ proportion.

The glass-ceramics according to the invention can be produced preferably by means of a method, in which
a) an initial glass is produced which comprises the components of the glass-ceramic,
b) the initial glass is subjected to a first heat treatment at a first temperature in order to produce a glass-ceramic which has lithium metasilicate as single or main crystal phase and
c) this glass-ceramic is subjected to a second heat treatment in which the lithium metasilicate is converted with $SiO_2$ from the glass phase into lithium disilicate and subsequently lithium disilicate is present as single or main crystal phase.

The crystallisation to form lithium metasilicate preferably takes place at temperatures between 620° C. and 800° C., with times between 1 and 200 minutes, preferably between 650° C. and 750° C. for 10 to 60 minutes.

The crystallisation to form lithium disilicate preferably takes place at temperatures between 800° C. and 1,040° C., with times of 5 to 200 minutes, preferably between 800° C. and 870° C. for 5 to 30 minutes.

The subject according to the invention is intended to be explained in more detail with reference to the subsequent examples without wishing to restrict said subject to the special embodiments shown here.

Examples 1 to 6

In examples 1 to 6, compositions of glasses with a high zirconium oxide content are indicated, which are converted by a two-step temperature treatment firstly into readily mechanically machinable lithium metasilicate glass-ceramics and subsequently into highly-translucent, very strong and chemically-stable lithium disilicate glass-ceramics.

The compositions with their components are represented in Table 1.

TABLE 1

|  | B1 | B2 | B3 | B4 | B5 | B6 |
| --- | --- | --- | --- | --- | --- | --- |
| $SiO_2$ | 66.9 | 65.8 | 65.5 | 63.7 | 63.5 | 63.5 |
| $Li_2O$ | 13.9 | 13.7 | 13.6 | 13.2 | 14.4 | 12.9 |
| $ZrO_2$ | 10.0 | 10.0 | 12.0 | 11.7 | 12.7 | 13.5 |
| $Al_2O_3$ | 3.2 | 3.1 | 3.1 | 3.0 | 3.3 | 3.5 |
| $P_2O_5$ | 3.0 | 3.0 | 3.0 | 2.9 | 3.1 | 3.4 |
| $K_2O$ | 2.9 | 2.9 | 2.9 | 2.8 | 3.0 | 3.2 |
| $CeO_2$ | — | 1.0 | — | 2.0 | — | — |
| $Er_2O_3$ | — | 0.2 | — | 0.3 | — | — |
| $Tb_2O_3$ | — | 0.3 | — | 0.3 | — | — |

The glasses were melted at 1,500° C. and poured into metal moulds to form blocks. The blocks were stress-relieved at 560° C. in the furnace and cooled slowly. For the different characterisation processes, the glass blocks were divided up and subjected to a first crystallisation treatment. For this purpose, the glasses were aged for 10 to 120 minutes at 600° C. to 750° C. As a result, glass-ceramics with strength values of 150 MPa to 220 MPa were produced. Exclusively lithium metasilicate was hereby established as crystal phase. In this state, machining by means of CAD/CAM methods is very readily possible.

With a second short crystallisation at 800° C. to 950° C. for 3 to 15 minutes, recrystallisation of the lithium metasilicate with amorphous $SiO_2$ from the glass phase takes place to form lithium disilicate and the result is an increase in strength to 300 MPa to 450 MPa. In addition to the lithium disilicate phase, a subsidiary crystal phase with a zirconium oxide content can hereby be produced. In addition, also small residues of lithium metasilicate can be present. The unequivocal main crystal phase is lithium disilicate.

In Table 2, the crystallisation conditions of individual glasses and also the resulting crystal phases and strength values are displayed.

TABLE 2

| Glass | B1 | B2 | B3 | B4 | B5 | B6 |
| --- | --- | --- | --- | --- | --- | --- |
| 1. Crystallisation | 650° C. 20 min | 700° C. 40 min | 650° C. 30 min | 700° C. 20 min | 700° C. 40 min | 700° C. 40 min |
| 2. Crystallisation | 850° C. 10 min | 830° C. 10 min | 870° C. 20 min | 850° C. 8 min | 820° C. 10 min | 830° C. 10 min |
| Crystal phases |  |  |  |  |  |  |
| Main phase (>80%) | di-silicate | di-silicate | di-silicate | di-silicate | di-silicate | di-silicate |
| Subsidiary phase (<20%) | — | — | — | — | meta-silicate | meta-silicate |
| Translucence | excellent | very good | excellent | very good | excellent | excellent |
| 3-point bending strength | 375 MPa | 413 MPa | 380 MPa | 418 MPa | 356 MPa | 385 MPa |

The invention claimed is:

1. A lithium silicate glass-ceramic having lithium disilicate as main crystal phase, comprising:
   58 to 64% by weight of $SiO_2$,
   11 to 13% by weight of $Li_2O$,
   10 to 15% by weight of a stabiliser selected from the group consisting of $ZrO_2$, $HfO_2$ and mixtures thereof,
   2 to 5% by weight of $K_2O$,
   2 to 5% by weight of $Al_2O_3$,
   0 to 5% by weight of additives selected from the group consisting of boron oxide, phosphorus oxide, fluorine, sodium oxide, barium oxide, strontium oxide, magnesium oxide, zinc oxide, calcium oxide, yttrium oxide, titanium oxide, niobium oxide, tantalum oxide, lanthanum oxide and mixtures thereof, and
   0 to 10% by weight of colourants.

2. The lithium silicate glass-ceramic according to claim 1, wherein the colourants are glass-colouring oxides and/or pigments.

3. The lithium silicate glass-ceramic according to claim 2, wherein the glass-colouring oxides are selected from the group consisting of oxides of iron, titanium, cerium, copper, chromium, cobalt, nickel, manganese, selenium, silver, indium, gold, and rare earth metals.

4. The lithium silicate glass-ceramic according to claim 3, wherein the rare earth metals are selected from the group consisting of neodymium, praseodymium, samarium and europium.

5. The lithium silicate glass-ceramic according to claim 2, wherein the pigments are doped spinels.

6. A method for the production of a lithium silicate glass-ceramic of claim 1, comprising the steps of:
   a) producing an initial glass which comprises the composition of:
      58 to 64% by weight of $SiO_2$,
      11 to 13% by weight of $Li_2O$, 10 to 15% by weight of the stabiliser selected from the group consisting of $ZrO_2$, $HfO_2$ and mixtures thereof,
2 to 5% by weight of $K_2O$,
2 to 5% by weight of $Al_2O_3$,
0 to 5% by weight of additives selected from the group consisting of boron oxide, phosphorus oxide, fluorine, sodium oxide, barium oxide, strontium oxide, magnesium oxide, zinc oxide, calcium oxide, yttrium oxide, titanium oxide, niobium oxide, tantalum oxide, lanthanum oxide and mixtures thereof, and
0 to 10% by weight of colourants,
b) subjecting the initial glass to a first heat treatment in order to produce a glass-ceramic which has lithium metasilicate as main crystal phase,
c) subjecting the glass-ceramic of b) to a second heat treatment in which the lithium metasilicate is converted with $SiO_2$ from the initial glass into lithium disilicate and subsequently lithium disilicate is present as main crystal phase.

7. The method according to claim 6, wherein the first heat treatment is effected at a temperature of 620° C. to 800° C. over a period of time of 1 to 200 min.

8. The method according to claim 7, wherein the second heat treatment is effected at a temperature of 800° C. to 1,040° C. over a period of time of 5 to 200 min.

9. A dental material comprising the lithium silicate glass-ceramic according to claim 1.

10. A shaped dental product comprising the lithium silicate glass-ceramic according to claim 1.

11. The shaped dental product according claim 10, which is an inlay, an onlay, a bridge, a pin construction, a veneer, or a crown.

* * * * *